US006087351A

United States Patent [19]

Nyce

[11] Patent Number: 6,087,351
[45] Date of Patent: Jul. 11, 2000

[54] METHOD FOR REDUCING ADENOSINE LEVELS WITH A DEHYDROEPIANDROSTERONE AND OPTIONALLY A UBIQUINONE

[75] Inventor: Jonathan W. Nyce, Greenville, N.C.

[73] Assignee: East Carolina University, Greenville, N.C.

[21] Appl. No.: 08/861,962

[22] Filed: May 22, 1997

Related U.S. Application Data

[62] Division of application No. 08/393,863, Feb. 24, 1995, Pat. No. 5,660,835.

[51] Int. Cl.[7] .................................................. A61K 31/56
[52] U.S. Cl. ........................... 514/178; 514/688; 514/826
[58] Field of Search .................................. 514/170, 177, 514/178, 182, 688, 826

[56] References Cited

U.S. PATENT DOCUMENTS

| | | | |
|---|---|---|---|
| 4,393,066 | 7/1983 | Garrett et al. | 424/251 |
| 4,499,064 | 2/1985 | Shive | 424/2 |
| 4,575,498 | 3/1986 | Holmes et al. | 514/43 |
| 4,628,052 | 12/1986 | Peat | 514/171 |
| 4,920,115 | 4/1990 | Nestler et al. | 514/178 |
| 4,931,441 | 6/1990 | Lawrence | 514/249 |
| 4,985,443 | 1/1991 | Montes | 514/249 |
| 5,021,417 | 6/1991 | Prost | 514/249 |
| 5,059,595 | 10/1991 | Le Grazie | 424/468 |
| 5,077,284 | 12/1991 | Loria et al. | 514/171 |
| 5,110,810 | 5/1992 | Eich et al. | 514/178 |
| 5,118,505 | 6/1992 | Költringer | 424/195.1 |
| 5,162,198 | 11/1992 | Eich et al. | 435/2 |
| 5,173,488 | 12/1992 | Haeger | 514/249 |
| 5,177,076 | 1/1993 | Nijkerk et al. | 514/249 |
| 5,266,312 | 11/1993 | Leung et al. | 424/85.5 |
| 5,270,305 | 12/1993 | Palmer | 514/171 |
| 5,347,075 | 9/1994 | Mueller et al. | 544/258 |
| 5,407,684 | 4/1995 | Loria et al. | 424/442 |
| 5,407,927 | 4/1995 | Morales et al. | 514/177 |
| 5,489,581 | 2/1996 | Daynes et al. | 514/170 |
| 5,527,789 | 6/1996 | Nyce | 514/178 |
| 5,532,230 | 7/1996 | Daynes et al. | 514/178 |
| 5,538,734 | 7/1996 | Le Grazie | 424/436 |
| 5,583,126 | 12/1996 | Daynes et al. | 514/178 |
| 5,635,496 | 6/1997 | Daynes et al. | 514/169 |
| 5,686,438 | 11/1997 | Daynes et al. | 514/178 |
| 5,811,418 | 9/1998 | Daynes et al. | 514/178 |
| 5,948,434 | 9/1999 | Labrie | 424/449 |

OTHER PUBLICATIONS

Itagaki et al.; "Effect of Cortisol on the Release of Human Decidual"; *Caplus*, 114875 (1991), Abstract.

Lejeune; "Pathogenesis of Mental Impairment in Trisomy 21"; *Biosis*, 92:27643 (1996) Abstract.

Peeters et al.; "Differences in Purine Metabolism in Patients with Down's Syndrome"; *Biosis*, 97125039 (1996) Abstract.

Mileva et al.; "Androstenedione, DHEA sulfate, cortisol, aldosterone and testosterone in bronchial asthma patients"; 07608054 (1990) Abstract.

Feher et al.; "Adrenocortical Function in Bronchial Asthma"; 05219963 (1983) Abstract.

Koo et al.; "Experiences with Dehydroepiandrosterone Therapy in Steroid–Dependent Intrinsic Bronchial Asthma"; *Biosis*, 85019995 (1987) Abstract.

Sur et al.; "Double–blind trial pyroxidine (vitamin B6) in the treatment of steroid–dependent asthma"; *Annals of Allergy*, 70:147–152 (1993).

Rowe et al.; "Effectiveness of Steroid Therapy in Acute Exacerbations of Asthma: A Meta–analysis"; *Amer J. of Emergency Medicine*, 10(4):301–310 (1992).

Van de Graaf et al.; "Respiratory Membrane Permeability and Bronchial Hyperreactivity in Patients with Stable Asthma: Effects of Therapy with Inhaled Steroids"; *Bronchial Asthma and Respiratory Membrane Permeability*, 143:362–368 (1991).

Hummel et al.; "Comparison of oral–steroid sparing by high–dose and low–dose inhaled steroid in maintenance treatment of severe asthma"; *The Lancet*, 340(8834/8835); 1483–1487 (1992).

Dompeling et al.; "Treatment with Inhaled Steroids in Asthma and Chronic Bronchitis: Long Term Compliance and Inhaler Technique"; *Family Practice—An International Journal*, pp. 161–166 (1992).

Coleridge et al.; "Intravenous aminophylline confers no benefit in acute asthma treated with intravenous steroids and inhaled bronchodilators"; *Medicine*, 23:348–354 (1993).

Dworski et al.; "Conspectus: Inhaled Steroids in Asthma"; *Comprehensive Therapy*, 18:3 (1992).

C. Reed; "Aerosol Steroids as Primary Treatment of Mild Asthma"; *The New England J. of Med.*, 325(6):425–426 (1991).

Sonka et al. Gout and Dehydroepiandrosterone. 3. DHEA Administration. Endokrynol–Pol. 24(3): pp. 209–218. May–Jun. 1973. Medline Citation Only.

Holzmann et al. Therapy of Psoriasis with Dehydroepiandrosterone–Enanthate. II. Intramuscular Depot Application of 300 mg. Weekly. Arch–Dermatol–Forsch. 247(1):pp. 23–28 (1973). Citation Only.

Sasaki et al. Cervical Ripening with Dehydroepiandrosterone Sulphate. Br–J Obstet–Gynaecol. 89(3): pp. 195–198. Mar. 1982, Medline Citation Only.

Pashko et al. Inhibition of 7,12–dimethylbenz(a)anthracene–induced Skin Papillomas and Carcinomas by Dehydroepiandrosterone and 3–beta–methylandrost–5–en–17–one in mice. Cancer Res. 45(1):164–6.

Araneo et al. Dehydroepiandrosterone Reduces Progressive Dermal Ischemia Caused by Thermal Injury. J–Surg–Res. 59(2): pp. 250–262. Aug. 1995. Medline Citation Only.

(List continued on next page.)

*Primary Examiner*—Robert H. Harrison
*Attorney, Agent, or Firm*—Viviana Amzel; Arter & Hadden LLP

[57] ABSTRACT

A method and composition for reducing adenosine levels comprises administering a dehydroepiandrosterone, and optionally a ubiquinone.

72 Claims, No Drawings

OTHER PUBLICATIONS

Van–Vollenhoven et al. DHEA in SLE. Results of a Double–Blind, Placebo–Controlled, Randomized Clinical Trial. Arthritis–Rheum. 38(12): pp. 1826–1831. Dec. 1995. Medline Citation Only.

Wolkowitz et al. DHEA Treatment of Depression. Biol–Psychiatry. 41(3): pp. 311–318. Feb. 1, 1997. Medline Citation Only.

Shomali.M.E. The Use of Anti–Aging Hormones. Melatonin. Growth Hormone, Testosterone, and Dehydroepiandrosterone: Consumer Enthusiasm for Unproven Therapies. Md–Med–J. 46(4):181–6. Cit.

Koo et al.; "Experiences with DHEA Therapy in Steroid–Dependent Intrinsic Bronchical Asthma"; Orvosi Hetilap; 128(38) pp. 1995–1997, 1987.

METHOD FOR REDUCING ADENOSINE LEVELS WITH A DEHYDROEPIANDROSTERONE AND OPTIONALLY A UBIQUINONE

RELATED APPLICATIONS

This application is a divisional of U.S. patent application Ser. No. 08/393,863, filed Feb. 24, 1995, U.S. Pat. No. 5,660,835.

FEDERALLY SPONSORED RESEARCH

This invention was made with Government support under Grant No. CA42217, awarded by the National Cancer Institute. The Government has certain rights in the invention.

FIELD OF THE INVENTION

This invention concerns itself with a method of treating adenosine depletion by administration of folinic acid or a pharmaceutically acceptable salt thereof. This invention further concerns itself with a method of treating asthma by administering dehydroepiandrosterone, analogs thereof, or their pharmaceutically acceptable salts.

DESCRIPTION OF THE BACKGROUND

Adenosine is a purine which contributes to intermediary metabolism and participates in the regulation of physiological activity in a variety of mammalian tissues. Adenosine participates in many local regulatory mechanisms, such as those occurring in synapses in the central nervous system (CNS) and at neuroeffector junctions in the peripheral nervous system. In the CNS, adenosine inhibits the release of a variety of neurotransmitters, such as acetylcholine, noradrenaline, dopamine, serotonin, glutamate, and GABA; depresses neurotransmission; reduces neuronal firing to induce spinal analgesia and possesses anxiolytic properties. See A. Pelleg and R. Porter, *Pharmacotherapy* 10(2), 157 (1990); J. Daval, et al., *Life Sciences* 49: 1435 (1991). In the heart, adenosine suppresses pacemaker activity, slows AV conduction, possesses antiarrhythmic and arrhythmogenic effects, modulates autonomic control and triggers the synthesis and release of prostaglandins. See K. Mullane and M. William, *Adenosine and Adenosine Receptors* p. 289 (M. Williams, ed. Humana Press, 1990). In addition, adenosine has potent vasodilatory effects and modulates vascular tone. See A Deuseen et al., *J. Pflugers Arch.* 406: 608 (1986). Adenosine is currently being used clinically for the treatment of superventricular tachycardia and other cardiac anomalies. See C. Chronister, *American Journal of Critical Care* 2(1): 41–47 (1993). Adenosine analogues are also being investigated for use as anticonvulsant, anxiolytic and neuroprotective agents. See M. Higgins et al., *Pharmacy World & Science* 16(2): 62–68 (1994).

Adenosine has also been implicated as a primary determinant underlying the symptoms of bronchial asthma. It induces bronchoconstriction and the contraction of airway smooth muscle. See J. Thorne and K. Broadley, *American Journal of Respiratory & Critical Care Medicine* 149(2 pt. 1): 392–399 (1994); S. Ali et al., *Agents & Actions* 37(3–4): 165–167 (1992). Adenosine causes bronchoconstriction in asthmatics but not in non-asthmatics. See Bjorck et al., *American Review of Respiratory Disease* 145(5): 1087–1091 (1992); S. Holgate et al., *Annals of the New York Academy of Sciences* 629: 227–236 (1991).

In view of the foregoing, it is readily apparent that (i) adenosine depletion may lead to a broad variety of deleterious conditions, and that methods of treating adenosine depletion may be an extremely useful means of therapeutic intervention; and (ii) methods of inducing adenosine depletion may also be useful in treating conditions such as asthma. Folinic acid is an intermediate product of the metabolism of folic acid; the active form into which that acid is converted in the body. Ascorbic acid is required as a necessary factor in the conversion process. Folinic acid has been used therapeutically as an antidote to folic acid antagonists such as methotrexate which block the conversion of folic acid into folinic acid. Additionally, folinic acid has been used as an anti-anemic (combatting folate deficiency). See The Merck Index, Monograph No. 4141 (11th Ed. 1989). The use of folinic acid in patients afflicted with adenosine depletion, or in a method to therapeutically elevate adenosine levels in the brain or other organ, has heretofor neither been suggested nor described.

SUMMARY OF THE INVENTION

The present invention relates to a method of treating adenosine depletion in a subject in need of such treatment. Which comprises administering to the subject folinic acid or a pharmaceutically acceptable salt thereof in an amount effective to treat the adenosine depletion. The method may be applied to subjects afflicted with steroid-induced adenosine depletion, subjects afflicted with anxiety, subjects afflicted with a wasting disorder, or subjects afflicted with any other disorder attributable to adenosine depletion, or where an increase in adenosine levels would be therapeutically beneficial.

The present invention also relates to the use of folinic acid or a pharmaceutically acceptable salt thereof for the preparation of a medicament for treating adenosine depletion in a subject in need of such treatment, as set forth above.

The present invention, moreover, relates to a method of treating asthma in a subject in need of such treatment by administering to the subject dehydroepiandrosterone, an analog thereof, or a pharmaceutically acceptable salt thereof, in an amount effective to treat asthma.

The present invention also relates to the use of dehydroepiandrosterone, an analog thereof, or a pharmaceutically acceptable salt thereof, for the manufacture of a medicament for treating asthma.

DETAILED DESCRIPTION OF THE PREFERRED EMBODIMENTS

The method of treating adenosine depletion disclosed herein may be used to treat steroid-induced adenosine depletion; to stimulate adenosine synthesis and thereby treat or control anxiety (e.g., in treating premenstrual syndrome); to increase weight gain or treat wasting disorders; and to treat other adenosine-related pathologies by administering folinic acid. Thus, the term "adenosine depletion" is intended to encompass both conditions where adenosine levels are depleted in the subject as compared to previous adenosine levels in that subject, and conditions where adenosine levels are essentially the same as previous adenosine levels in that subject but, because of some other condition or alteration in that patient, a therapeutic benefit would be achieved in the patient by increased adenosine levels as compared to previous levels. Preferably, the method is carried out on patients where adenosine levels are depleted as compared to previous adenosine levels in that subject. The present invention is concerned primarily with the treatment of human subjects but may also be employed for the treatment of other mammalian subjects, such as dogs and cats, for veterinary purposes.

Folinic acid and the pharmaceutically acceptable salts thereof (hereafter sometimes referred to as "active compounds") are known, and can be made in accordance with known procedures. See generally The Merck Index, Monograph No. 4141 (11th Ed. 1989); U.S. Pat. No. 2,741,608.

Pharmaceutically acceptable salts should be both pharmacologically and pharmaceutically acceptable. Such pharmacologically and pharmaceutically acceptable salts can be prepared as alkaline metal or alkaline earth salts, such as sodium, potassium or calcium salts, of the carboxylic acid group of Folinic acid. The calcium salt of folinic acid is a preferred pharmaceutically acceptable salt.

The active compounds are preferably administered to the subject as a pharmaceutical composition. Pharmaceutical compositions for use in the present invention include those suitable for inhalation, oral, topical, (including buccal, sublingual, dermal and intraocular) parenteral (including subcutaneous, intradermal, intramuscular, intravenous and intraarticular) and transdermal administration. The compositions may conveniently be presented in unit dosage form and may be prepared by any of the methods well known in the art.

Compositions suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such compositions may be prepared by any suitable method of pharmacy which includes the step of bringing into association the active compound and a suitable carrier. In general, the compositions of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder. Compositions for oral administration may optionally include enteric coatings known in the art to prevent degradation of the compositions in the stomach and provide release of the drug in the small intestine.

Compositions suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Compositions suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the compositions isotonic with the blood of the intended recipient. Aqueous and non-aqueous sterile suspensions may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

Compositions suitable for topical application to the skin preferably take the form of an ointment, cream, lotion, paste, gel, spray, aerosol, or oil. Carriers which may be used include vaseline, lanoline, polyethylene glycols, alcohols, transdermal enhancers, and combinations of two or more thereof.

Compositions suitable for transdermal administration may be presented as discrete patches adapted to remain in intimate contact with the epidermis of the recipient for a prolonged period of time. Compositions suitable for transdermal administration may also be delivered by iontophoresis (see, e.g., *Pharmaceutical Research* 3, 318 (1986)) and typically take the form of an optionally buffered aqueous solution of the active compound.

Dosage will vary depending on age, weight, and condition of the subject. Treatment may be initiated with small dosages less than optimum dose and increased until the optimum effect under the circumstances is reached. In general, the dosage will be from 1, 5, 10 or 20 mg/kg subject body weight, up to 100, 200, 500 or 1000 mg/kg subject body weight. Currently, dosages of from 5 to 500 mg/kg are preferred, dosages of from 10 to 200 mg/kg are more preferred, and dosages of from 20 to 100 mg/kg are most preferred. In general, the active compounds are preferably administered at a concentration that will afford effective results without causing any unduly harmful or deleterious side effects, and may be administered either as a single unit dose, or if desired, in convenient subunits administered at suitable times throughout the day.

Also disclosed herein is a method of reducing adenosine levels, particularly in the lung, liver and brain, as shown in Table 1 for a rat animal model and, therefore, for treating asthma, particularly non-steroid dependent asthma, by administering to a subject in need of such treatment debydroepiandrosterone (DHEA), an analog thereof, or a pharmaceutically acceptable salt thereof, in an amount effective to inibit or control asthma to that subject. Examples of DHEA and analogs thereof that may be used to carry out this method are represented by the formula:

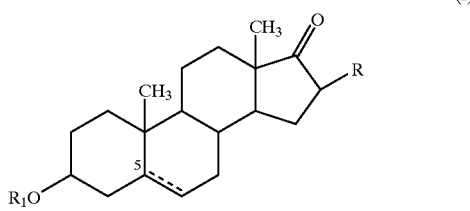

wherein:

the broken line represents an optional double bond;

R is hydrogen or a halogen;

$R_1$ is hydrogen or an $SO_2OM$ group where M is hydrogen, M is sodium, M is a sulphatide group:

$$-SO_2O-CH_2CHCH_2OCOR_3$$
$$|$$
$$OCOR_2$$

M is a phosphatide group:

$$-\overset{O}{\underset{\underset{O}{\|}}{\overset{\|}{P}}}-OCH_2CHCH_2OCOR_3$$
$$\phantom{-P-OCH_2CH}|$$
$$\phantom{-P-OCH_2CH}OCOR_2$$

wherein each of $R_2$ and $R_3$, which may be the same or different, is a straight or branched chain alkyl radical of 1 to 14 carbon atoms, or a glucuronide group:

[structure of glucuronide group with COOH, OH, HO substituents on a pyranose ring]

The hydrogen atom at position 5 of Formula I is present in the alpha or beta configuration or the compound comprises a mixture of both configurations. Compounds illustrative of Formula (I) above include:

DHEA, wherein R and $R_1$ are each hydrogen and the double bond is present;

16-alpha bromoepiandrosterone, wherein R is Br, $R_1$ is H, and the double bond is present;

16-alpha-fluoroepiandrosterone, wherein R is F, $R_1$ is H and the double bond is present;

etiocholanolone, wherein R and $R_1$ are each hydrogen and the double bond is absent;

dehydroepiandrosterone sulphate, wherein R is H, $R_1$ is $SO_2OM$ and M is a sulphatide group as defined above, and the double bond absent. Preferably, in the compound of Formula I, R is halogen (e.g., bromo, chloro, or fluoro), $R_1$ is Hydrogen, and the double bond is present. Most preferably the compound of Formula I is 16-alpha-fluoroepiandrosterone.

The compounds of Formula I are made in accordance with known procedures or variations thereof that will be apparent to those skilled in the art. See U.S. Pat. No. 4,956,355, UK Patent No. 2,240,472, EPO Patent Appln No. 429,187, PCT Patent Appln No. 91/04030; see also M. Abou-Gharbia et al., *J. Pharm. Sci.* 70, 1154–1157 (1981), Merck Index Monograph No. 7710 (11th ed. 1989).

The compounds used to treat asthma may be administered per se or in the form of pharmaceutically acceptable salts, as discussed above (the two together again being referred to as "active compounds"). The active compounds salts may be administered either systemically, as discussed above, or to the lungs of the subject as discussed below. In general, the active compounds salts are administered in a dosage of 1 to 3600 mg/kg body weight, more preferably about 5 to 1800 mg/kg, and most preferably about 20 to 100 mg/kg. The active compounds may be administered once or several times a day.

The active compounds disclosed herein may be administered to the lungs of a subject by any suitable means, but are preferably administered by generating an aerosol comprised of respirable particles, the respirable particles comprised of the active compound, which particles the subject inhales (i.e., by inhalation administration). The respirable particles may be liquid or solid.

Particles comprised of active compound for practicing the present invention should include particles of respirable size: that is, particles of a size sufficiently small to pass through the mouth and larynx upon inhalation and into the bronchi and alveoli of the lungs. In general, particles ranging from about 0.5 to 10 microns in size (more particularly, less than about 5 microns in size) are respirable. Particles of non-respirable size which are included in the aerosol tend to deposit in the throat and be swallowed, and the quantity of non-respirable particles in the aerosol is preferably minimized. For nasal administration, a particle size in the range of 10–500 $\mu$m is preferred to ensure retention in the nasal cavity.

Liquid pharmaceutical compositions of active compound for producing an aerosol may be prepared by combining the active compound with a suitable vehicle, such as sterile pyrogen free water. Solid particulate compositions containing respirable dry particles of micronized active compound may be prepared by grinding dry active compound with a mortar and pestle, and then passing the micronized composition through a 400 mesh screen to break up or separate out large agglomerates. A solid particulate composition comprised of the active compound may optionally contain a dispersant which serves to facilitate the formation of an aerosol. A suitable dispersant is lactose, which may be blended with the active compound in any suitable ratio (e.g., a 1 to 1 ratio by weight).

Aerosols of liquid particles comprising the active compound may be produced by any suitable means, such as with a nebulizer. See, e.g., U.S. Pat. No. 4,501,729. Nebulizers are commercially available devices which transform solutions or suspensions of the active ingredient into a therapeutic aerosol mist either by means of acceleration of a compressed gas, typically air or oxygen, through a narrow venturi orifice or by means of ultrasonic agitation. Suitable compositions for use in nebulizers consist of the active ingredient in a liquid carrier, the active ingredient comprising up to 40% w/w of the compositions, but preferably less than 20% w/w. the carrier is typically water or a dilute aqueous alcoholic solution, preferably made isotonic with body fluids by the addition of, for example, sodium chloride. Optional additives include preservatives if the compositions is not prepared sterile, for example, methyl hydroxybenzoate, antioxidants, flavoring agents, volatile oils, buffering agents and surfactants.

Aerosols of solid particles comprising the active compound may likewise be produced with any solid particulate medicament aerosol generator. Aerosol generators for administering solid particulate medicaments to a subject produce particles which are respirable, as explained above, and generate a volume of aerosol containing a predetermined metered dose of a medicament at a rate suitable for human administration. Examples of such aerosol generators include metered dose inhalers and insufflators.

Ubiquinone may be administered concurrently with the DHEA or analog thereof in the methods of treating asthma described above. The phrase "concurrently administering," as used herein, means that the DHEA or the DHEA analog are administered either (a) simultaneously in time (preferably by formulating the two together in a common pharmaceutical carrier), or (b) at different times during the course of a common treatment schedule. In the latter case, the two compounds are administered at times sufficiently close for the ubiquinone to ubiquinone depletion in the lungs (and heart) of the subject and thereby counterbalance any deterioration of lung (and heart) function that may result from the administration of the DHEA or the analog thereof. The term "ubiquinoneu", as used herein, refers to a family of compounds having structures based on a 2,3-dimethoxy-5-methylbenzoquinone nucleus with a variable terpenoid acid chain containing on to twelve mono-unsaturated trans-isoprenoid units. Such compounds are known in the art as "Coenzyme $Q_n$", in which n equals 1 to 12. These compounds may be referred to herein as compounds represented by the formula:

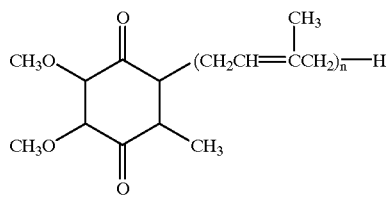

wherein n=1 to 10. Preferably, in the method of the invention, the ubiquinone is a compound according to formula given above, wherein n=6 to 10 (e.g., Coenzymes $Q_{6-10}$) and most preferably wherein n=10 (i.e., Coenzyme $Q_{10}$).

Where the ubiquinone is formulated with a pharmaceutically acceptable carrier separately from the DHEA, analog thereof, or salt thereof (e.g., where the DHEA, analog thereof or salt thereof is administered to the lungs of the subject, and the ubiquinone is administered systemically) it may be formulated by any of the techniques set forth above.

In general, the ubiquinone is administered in an amount effective to offset ubiquinone depletion in the lungs and heart of the subject induced by the DHEA, analog thereof, or salt thereof, and the dosage will vary depending upon the condition of the subject and the route of administration. The ubiquinone is preferably administered in a total amount per day of about 1 to 1200 mg/kg body weight, more preferably about 30 to 600 mg/kg, and most preferably about 50 to 150 mg/kg. The ubiquinone may be administered once or several times a day.

The following examples are provided to more fully illustrate the present invention and should not be construed as restrictive thereof. In the following examples, DHEA means dehydroepiandrosterone, s means seconds, mg means milligrams, kg means kilograms, kW means kilowatts, MHz means megahertz, and nmol means nanomoles.

EXAMPLES 1 AND 2

Effects of Folinic Acid and DHEA on Adenosine Levels In vivo

Young adult male Fischer 344 rats (120 grams) were administered dehydroepiandrosterone (DHEA) (300 mg/kg) or methyltestosterone (40 mg/kg) in carboxymethylcellulose by gavage once daily for fourteen days. Folinic acid (50 mg/kg) was administered intraperitoneally once daily for fourteen days. On the fifteenth day, the animals were sacrificed by microwave pulse (1.33 kW, 2450 MHz, 6.5 s) to the cranium, which instantly denatures all brain protein and prevents further metabolism of adenosine. Hearts were removed from animals and flash frozen in liquid nitrogen within 10 seconds of death. Liver and lungs were removed en bloc and flash frozen within 30 seconds of death. Brain tissue was subsequently dissected. Tissue adenosine was extracted, derivatized to 1,$N^6$-ethenoadenosine and analyzed by high performance liquid chromatography (HPLC) using spectrofluorometric detection according to the method of Clark and Dar (*J. of Neuroscience Methods* 25: 243 (1988)). Results of these experiments are summarized in Table 1 below. Results are expressed as the mean ± SEM, with $\chi$ $p<0.05$ compared to control group and $\phi$ $p<0.05$ compared to DHEA or methyltestosterone-treated groups.

TABLE 1

Effects of DHEA, δ-1-methyltestosterone and folinic acid on adenosine levels in various tissues of the rat.

| Treatment | Intracellular adenosine (nmols)/mg protein | | | |
|---|---|---|---|---|
| | Heart | Liver | Lung | Brain |
| Control | 10.6 ± 0.6 (n = 12) | 14.5 ± 1.0 (n = 12) | 3.1 ± 0.2 (n = 6) | 0.5 ± 0.04 (n = 12) |
| DHEA (300 mg/kg) | 6.7 ± 0.5 (n = 12)ψ | 16.4 ± 1.4 (n = 12) | 2.3 ± 0.3 (n = 6)ψ | 0.19 ± 0.01 (n = 12)ψ |
| Methyltestosterone (40 mg/kg) | 8.3 ± 1.0 (n = 6)ψ | 16.5 ± 0.9 (n = 6) | N.D. | 0.42 ± 0.06 (n = 6) |
| Methyltestosterone (120 mg/kg) | 6.0 ± 0.4 (n = 6)ψ | 5.1 ± 0.5 (n = 6)ψ | N.D. | 0.32 ±0.03 (n = 6)ψ |
| Folinic Acid (50 mg/kg) | 12.4 ± 2.1 (n = 5) | 16.4 ± 2.4 (n = 5) | N.D. | 0.72 ± 0.09 (n = 5)ψ |
| DHEA (300 mg/kg) + Folinic Acid (50 mg/kg) | 11.1 ± 0.6 (n = 5)φ | 18.8 ± 1.5 (n = 5)φ | N.D. | 0.55 ± 0.09 (n = 5)φ |
| Methyltestosterone (120 mg/kg) + Folinic Acid (50 mg/kg) | 9.1 ± 0.4 (n = 6)φ | N.D. | N.D. | 0.60 ± 0.06 (n = 6)φ |

The results of these experiments indicate that rats administered DHEA or methyltestosterone daily for two weeks showed multi-organ depletion of adenosine. Depletion was dramatic in brain (60% depletion for DHEA, 34% for high dose methyltestosterone) and heart (37% depletion for DHEA, 22% depletion for high dose methyltestosterone). Co-administration of folinic acid completely abrogated steroid-mediated adenosine depletion. Folinic acid administered alone induce increases in adenosine levels for all organs studied.

The foregoing examples are illustrative of the present invention, and are not to be construed as limiting thereof. The invention is defined by the following claims, with equivalents of the claims to be included therein.

That which is claimed is:

1. An in vivo method of reducing or depleting adenosine in a subject's tissue (s), comprising administering to a subject in need of treatment an amount of an agent effective to reduce or deplete adenosine levels in a subject's tissue (s); the agent being selected from the group consisting of a dehydrepiandrosterone of the chemical formula

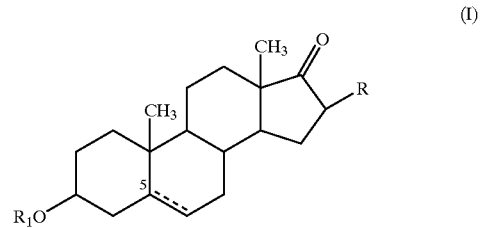

(I)

wherein
the broken line represents a single or a double bond;
R is hydrogen or a halogen;
the H at position 5 is present in the alpha or beta configuration or the compound of formula I comprises a racemic mixture of both configurations; and
$R^1$ is hydrogen or $SO_2OM$, wherein M is selected from the group consisting of H, Na, sulphatide

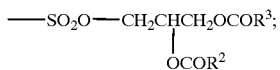

and phosphatide

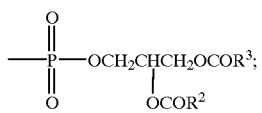

wherein
$R^2$ and $R^3$, which may be the same or different, are straight or branched $(C_1-C_{14})$ alkyl or glucuronide

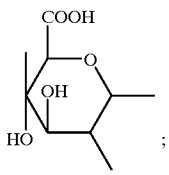

and
pharmaceutically acceptable salts thereof.

2. The method of claim 1, wherein the compound of formula (I) is dimethyl epiandosterone (DMEA) or dehydroepiandrosterone, wherein R and $R^1$ are both $CH_3$ or H, respectively, and the broken line represents a double bond.

3. The method of claim 1, wherein the compound of formula I is 16-alpha bromoepiandrosterone, wherein R is Br, $R^1$ is H, and the broken line represents a double bond.

4. The method of claim 1, wherein the compound of formula I is 16-alpha-fluoro epiandrosterone, wherein R is F, $R^1$ is H and broken line represents a double bond.

5. The method of claim 1, wherein the compound of formula I is etiocholanolone, wherein R and $R^1$ are each hydrogen and the broken line represents a double bond.

6. The method of claim 1, wherein the compound of formula I is dehydroepiandrosterone sulphate, wherein R is H, $R^1$ is $SO_2OM$ and M is a sulphatide group as defined above, and the broken line represents a single bond.

7. The method of claim 1, wherein in the compound of formula I, R is halogen selected from the group consisting of Br, Cl and F, $R^1$ is H, and the broken line represents a double bond.

8. The method of claim 1, wherein the compound of formula I is 16-alpha-fluoro epiandrosterone.

9. The method of claim 1, wherein the compound of formula I is selected from the group consisting of dehydroepiandrosterone, 16-alpha-bromoepiandrosterone, 16-alpha-fluoro epiandrosterone, etiocholanolone, dehydroepiandrosterone sulphate and pharmaceutically acceptable salts thereof.

10. The method of claim 1, wherein the agent is administered systemically or topically.

11. The method of claim 10, wherein the agent is administered by a route selected from the group consisting of oral, inhalable, topical, parenteral, and transdermal routes.

12. The method of claim 11, wherein the agent is administered by an oral, inhalable, topical, parenteral or transdermal route selected from the group consisting of buccal, sublingual, dermal, intraocular, subcutaneous, intradermal, intramuscular, intravenous and intraarticular routes.

13. The method of claim 11, wherein the agent is administered as an oral formulation selected from the group consisting of capsules, cachets, lozenges, tablets, powder, granules, solutions, suspensions and emulsions.

14. The method of claim 13, wherein the solutions and suspensions are selected from the group consisting of aqueous and non-aqueous liquid solutions and suspensions.

15. The method of claim 13, wherein the emulsions are selected from the group consisting of oil-in-water and water-in-oil emulsions.

16. The method of claim 11, wherein the agent is administered as a buccal or sub-lingual formulation selected from the group consisting of
lozenges further comprising a flavoring agent selected from the group consisting of sucrose, acacia and tragacanth; and
pastilles further comprising an inert base selected from the group consisting of gelatin, glycerin, sucrose and acacia.

17. The method of claim 13, wherein the oral formulation further comprises an enteric coating.

18. The method of claim 11, wherein the agent is administered as a parenteral formulation selected from the group consisting of injectable solutions or suspensions, which may further comprise antioxidants, buffers, bacteriostatic agents and solutes which render the solution or suspension isotonic with the blood of any intended recipient.

19. The method of claim 18, wherein the solutions and suspensions are selected from the group consisting of sterile aqueous and non-aqueous injection solutions and suspensions, which may further comprise suspending agents and thickening agents.

20. The method of claim 10, in unit-dose form.

21. The method of claim 10, wherein the formulation is in bulk or multi-dose form.

22. The method of claim 18, wherein the parenteral formulation is provided in bulk or multi-dose form selected from the group consisting of sealed ampules and vials.

23. The method of claim 10, wherein the formulation is freeze-dried or lyophilized; and the method further comprises adding a sterile liquid carrier selected from the group consisting of saline and water prior to use.

24. The method of claim 11, wherein the agent is administered as a topical formulation selected from the group consisting of ointments, creams, lotions, pastes, gels, sprays, aerosols and oils; which may further comprise a carrier selected from the group consisting of vaseline, lanoline, polyethylene glycols, alcohols and trans-dermal enhancers.

25. The method of claim 11, wherein the agent is administered as a transdermal formulation by means of a device selected from the group consisting of a patch and a transdermal delivery device.

26. The method of claim 25, wherein the transdermal formulation is an iontophoretic formulation, and the delivery device is an iontophoretic device comprising a solution or suspension of the agent, which may further comprise a buffer.

27. The method of claim 11, wherein the agent is administered as an inhalable formulation.

28. The method of claim 27, wherein the inhalable formulation is an aerosol comprising liquid or solid particles of the agent, and which may further comprise preservatives, antioxidants, flavoring agents, volatile oils, buffering agents, dispersants or surfactants.

29. The method of claim 1, wherein the ant is administered in an amount of about 1 to 3,600 mg/kg body wt.

30. The method of claim 29, wherein the agent is administered in an amount of about 5 to 1,800 mg/kg body wt.

31. The method of claim 29, wherein the agent is administered in an amount of about 20 to 100 mg/kg body wt.

32. The method of claim 1, wherein the administration is conducted with a composition comprising up to about 40% w/w agent.

33. The method of claim 32, wherein the administration is conducted with a composition comprising less than about 40% w/w agent.

34. The method of claim 1, wherein the subject is a human.

35. The method of claim 1, wherein the subject is a non-human animal.

36. The method of claim 1, wherein, which is a prophylactic method.

37. The method of claim 1, which is a therapeutic method.

38. The method of claim 34, for preventing or treating non steroid-dependent asthma.

39. The method of claim 1, further comprising administering to the subject an amount of ubiquinone ($CoQ_n$, wherein n=1 to 12) effective to prevent, counter or reduce adenosine depletion in the subject's tissue(s).

40. The method of claim 39, wherein in the $CoQ_n$, wherein n=1 to 10.

41. The method of claim 40, wherein in the $CoQ_n$, wherein n=6 to 10.

42. The method of claim 41, wherein in the $CoQ_n$, wherein n=10.

43. The method of claim 39, wherein the ubiquinone is administered as a composition further comprising a pharmaceutically acceptable carrier.

44. The method of claim 43, wherein the ubiquinone composition further comprises an ingredient selected from the group consisting of preservatives, antioxidants, flavoring agents, volatile oils, buffering agents, dispersants or surfactants.

45. The method of claim 39, wherein the ubiquinone is administered in an amount of about 1 to about 1,200 mg/kg body weight.

46. The method of claim 45, wherein the ubiquinone is administered in an amount of about 30 to about 600 mg/kg body weight.

47. The method of claim 46, wherein the ubiquinone is administered in an amount of about 50 to about 180 mg/kg body weight.

48. The method of claim 39, wherein the ubiquinone is administered concurrently with the agent.

49. The method of claim 48, wherein the agent and the ubiquinone are administered in the same formulation.

50. The method of claim 18, wherein the agent is administered as a parenteral formulation selected from the group consisting of subcutaneous, intradermal, intramuscular, intravenous and intraarticular formulations.

51. The method of claim 1, wherein the composition further comprises a second agent selected from the group consisting of preservatives, antioxidants, flavoring agents, buffers, bacteriostatic agents, blood isotonic agents, volatile oils, buffering agents, dispersants and surfactants.

52. The method of claim 1, wherein the agent is administered as a composition further comprising a second agent selected from ubiquinones ($CoQ_n$), wherein n=1 to 12.

53. The method of claim 52, wherein the second agent comprises a $CoQ_n$, wherein n=1 to 10.

54. The method of claim 53, wherein the second agent comprises a $CoQ_n$, wherein n=6 to 10.

55. The method of claim 54, wherein the second agent comprises a $CoQ_n$, wherein n=10.

56. The method of claim 52, wherein the composition comprises about 1 to 1200 mg/day/kg body weight of the second agent.

57. The method of claim 56, wherein the composition comprises about 30 to 600 mg/day/kg body weight of the second agent.

58. The method of claim 57, wherein the composition comprises about 50 to 150 mg/day/kg body weight of the second agent.

59. The method of claim 10, wherein the agent is administered as a composition further comprising a carrier.

60. The method of claim 59, wherein the carrier is selected from the group consisting of solid and liquid carriers.

61. The method of claim 59, wherein the composition is a pharmaceutical or veterinary composition, and the carrier comprises a pharmaceutically or veterinarily acceptable carrier.

62. The method of claim 59, wherein the carrier comprises a hydrophobic carrier.

63. The method of claim 62, wherein the composition is administered by means of a delivery device.

64. The method of claim 63, wherein the composition is administered by a delivery device that comprises an inhalator.

65. The method of claim 64, wherein the inhalator comprises a nebulizer or insufflator, and the composition comprises solid particles of the agent(s) contained in a piercable or openable capsule or cartridge.

66. The method of claim 65, wherein the delivery device comprises a pressurized inhaler, and the composition comprises a suspension or solution in an aqueous or non-aqueous liquid or an oil-in-water or water-in-oil emulsion.

67. The method of claim 64, wherein the composition is delivered in a capsule.

68. The method of claim 59, wherein the composition further comprises a second agent selected from the group consisting of preservatives, antioxidants, flavoring agents, buffers, bacteriostatic agents, blood isotonic agents, volatile oils, buffering agents, dispersants and surfactants.

69. The method of claim 1, wherein the agent is administered as a composition further comprising a pharmaceutically or veterinarily acceptable carrier.

70. An in vivo method of preventing or treating a disorder or condition associated with high levels of, or high sensitivity to, adenosine in a subject's tissue (s), comprising applying to the subject the method of claim 19, wherein the amount of the agent administered to the subject is effective to reduce adenosine levels in the subject's tissue (s) and, thereby, prevent or treat the disorder or condition; wherein when the disease or condition is steroid-dependent asthma, the agent is the sole active compound.

71. The method of claim 70, wherein the disorder or condition is selected from the group consisting of disorders or conditions of the heart, liver, lung (s) and brain.

72. The method of claim 71, wherein the tissue is the subject's lung (s); the method is for preventing or treating steroid-dependent asthma; and the agent is the sole anti-asthmatic agent administered.

* * * * *